(12) United States Patent
Hoogervorst

(10) Patent No.: US 10,085,779 B2
(45) Date of Patent: Oct. 2, 2018

(54) INTRAMEDULLARY DEVICE FOR MID-SHAFT CLAVICLE FRACTURES

(71) Applicant: Stichting Katholieke Universiteit, Nijmegen (NL)

(72) Inventor: Paul Hoogervorst, Nijmegen (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 0 days.

(21) Appl. No.: 15/106,152

(22) PCT Filed: Dec. 3, 2014

(86) PCT No.: PCT/EP2014/076340
§ 371 (c)(1),
(2) Date: Jun. 17, 2016

(87) PCT Pub. No.: WO2015/090954
PCT Pub. Date: Jun. 25, 2015

(65) Prior Publication Data
US 2016/0317200 A1    Nov. 3, 2016

(30) Foreign Application Priority Data
Dec. 17, 2013 (EP) ..................... 13197625

(51) Int. Cl.
*A61B 17/56* (2006.01)
*A61B 17/58* (2006.01)
(Continued)

(52) U.S. Cl.
CPC ...... *A61B 17/7233* (2013.01); *A61B 17/7291* (2013.01); *A61B 17/863* (2013.01);
(Continued)

(58) Field of Classification Search
CPC .... A61B 17/72–17/7291; A61B 17/84–17/842
See application file for complete search history.

(56) References Cited

U.S. PATENT DOCUMENTS 3,986,504 A * 10/1976 Avila ................. A61B 17/7266
606/63
4,640,271 A * 2/1987 Lower ................ A61B 17/742
606/105
(Continued)

FOREIGN PATENT DOCUMENTS

DE    3924610    3/1990
WO    2011060412    5/2011

OTHER PUBLICATIONS

International Search Report PCT/EP2014/076340 dated Jan. 22, 2015.

*Primary Examiner* — Eduardo C Robert
*Assistant Examiner* — Michelle C Eckman
(74) *Attorney, Agent, or Firm* — Young & Thompson

(57) ABSTRACT

An intramedullary device for treatment of a mid-shaft clavicle fracture includes a base pin (1) having a primary fixation element (2) and a connection part (3). A secondary fixation element (6) is provided which is attachable to the connection part (3) at a distance along the base pin with respect to the primary fixation element (2). The connection part (3) of the base pin (1) and the secondary fixation element (6) are rotatable with respect to each other when attached, e.g. using an end cap (7).

23 Claims, 4 Drawing Sheets

(51) Int. Cl.
*A61F 2/30* (2006.01)
*A61B 17/72* (2006.01)
*A61B 17/86* (2006.01)
*A61B 17/92* (2006.01)

(52) U.S. Cl.
CPC ........ *A61B 17/8685* (2013.01); *A61B 17/921* (2013.01); *A61B 17/7225* (2013.01)

(56) References Cited

U.S. PATENT DOCUMENTS

| | | | | |
|---|---|---|---|---|
| RE33,348 E | * | 9/1990 | Lower | A61B 17/8685 606/304 |
| 5,374,235 A | * | 12/1994 | Ahrens | A61B 17/7233 606/101 |
| 5,417,692 A | * | 5/1995 | Goble | A61B 17/68 433/173 |
| 5,480,402 A | * | 1/1996 | Kim | A61B 17/1725 606/64 |
| 6,338,732 B1 | | 1/2002 | Yang | |
| 6,413,260 B1 | * | 7/2002 | Berrevoets | A61B 17/68 606/304 |
| 6,524,313 B1 | * | 2/2003 | Fassier | A61B 17/72 606/63 |
| 9,474,561 B2 | * | 10/2016 | Shemwell | A61B 17/7291 |
| 9,482,260 B1 | * | 11/2016 | Krause | F16B 35/041 |
| 9,615,873 B2 | * | 4/2017 | Weiner | A61B 17/8685 |
| 9,675,392 B2 | * | 6/2017 | Shemwell | A61B 17/7291 |
| 2002/0198527 A1 | * | 12/2002 | Muckter | A61B 17/8685 606/316 |
| 2004/0172031 A1 | * | 9/2004 | Rubecamp | A61B 17/8685 606/309 |
| 2005/0216007 A1 | * | 9/2005 | Woll | A61B 17/7225 606/62 |
| 2006/0264954 A1 | * | 11/2006 | Sweeney, II | A61B 17/8685 606/312 |
| 2007/0260248 A1 | * | 11/2007 | Tipirneni | A61B 17/68 606/65 |
| 2008/0147126 A1 | * | 6/2008 | Tipirneni | A61B 17/8869 606/300 |
| 2009/0216232 A1 | * | 8/2009 | Buford, III | A61B 5/107 606/62 |
| 2009/0306718 A1 | * | 12/2009 | Tipirneni | A61B 17/683 606/263 |
| 2010/0312292 A1 | * | 12/2010 | Tipirneni | A61B 17/92 606/86 R |
| 2011/0009865 A1 | | 1/2011 | Orfaly | |
| 2011/0034925 A1 | * | 2/2011 | Tipirneni | A61B 17/683 606/62 |
| 2011/0077651 A1 | * | 3/2011 | Lozier | A61B 17/7258 606/62 |
| 2011/0295252 A1 | * | 12/2011 | Tipirneni | A61B 17/685 606/62 |
| 2011/0301653 A1 | * | 12/2011 | Reed | A61B 17/1604 606/62 |
| 2012/0065692 A1 | * | 3/2012 | Champagne | A61B 17/7291 606/311 |
| 2013/0131678 A1 | * | 5/2013 | Dahners | A61B 17/7208 606/62 |
| 2013/0150965 A1 | * | 6/2013 | Taylor | A61F 2/30 623/16.11 |
| 2013/0158552 A1 | * | 6/2013 | Overes | A61B 17/7241 606/64 |
| 2013/0226191 A1 | * | 8/2013 | Thoren | A61B 17/8886 606/104 |
| 2013/0274814 A1 | * | 10/2013 | Weiner | A61B 17/1682 606/301 |
| 2014/0005728 A1 | * | 1/2014 | Koay | A61B 17/8057 606/281 |
| 2014/0052196 A1 | * | 2/2014 | McGinley | A61B 17/8605 606/319 |
| 2014/0142715 A1 | * | 5/2014 | McCormick | A61B 17/8883 623/21.19 |
| 2015/0012048 A1 | * | 1/2015 | Huebner | A61B 17/864 606/304 |
| 2015/0045839 A1 | * | 2/2015 | Dacosta | A61B 17/8897 606/305 |
| 2015/0112342 A1 | * | 4/2015 | Penzimer | A61B 17/8875 606/63 |
| 2015/0164563 A1 | * | 6/2015 | Lewis | A61F 2/4606 606/63 |
| 2015/0202413 A1 | * | 7/2015 | Lappin | A61B 17/8897 600/585 |
| 2015/0257800 A1 | * | 9/2015 | Harshman | A61B 17/7208 606/62 |
| 2016/0081727 A1 | * | 3/2016 | Munday | A61B 17/7225 606/62 |
| 2016/0256290 A1 | * | 9/2016 | Seavey | A61B 17/7291 |
| 2017/0100171 A1 | * | 4/2017 | Palmer | A61B 17/7225 |
| 2017/0112552 A1 | * | 4/2017 | Sinnott | A61B 17/7233 |
| 2017/0135737 A1 | * | 5/2017 | Krause | A61B 17/7225 |
| 2017/0156772 A1 | * | 6/2017 | Brinker | A61B 17/842 |
| 2017/0156877 A1 | * | 6/2017 | Reed | A61F 2/4225 |
| 2017/0164954 A1 | * | 6/2017 | Hayes | A61B 17/1655 |
| 2017/0189085 A1 | * | 7/2017 | Krause | A61B 17/7233 |

* cited by examiner

INTRAMEDULLARY DEVICE FOR MID-SHAFT CLAVICLE FRACTURES

FIELD OF THE INVENTION

The present invention relates to an intramedullary device for treatment of a fracture of a long pipe bone, such as a (mid-shaft) clavicle fracture.

PRIOR ART

U.S. Pat. No. 4,640,271 (Lower) discloses a bone screw having a main shaft and a separate sleeve member. The main shaft has a first set of threads on a leading end portion and an elongated smooth unthreaded shaft portion with a protruding lip on the opposite, trailing end of the main shaft. The separate sleeve member, provided with a second set of threads on its outer surface, is held in position by the protruding lip on the unthreaded shaft portion, but only in one direction. No axial stability is provided by the bone screw, and also no flexibility is provided.

US patent publication US 2009/306718 discloses a lagwire system for facilitating fixation of bone fractures An anchor component is provided as well as a wire, a threaded sleeve, a tubular sleeve and a cap. The lagwire system is only suitable for exerting a compressing force, and no rotation at the fixation position is possible.

U.S. Pat. No. 6,338,732 discloses an in marrow nail structure having a pin with two threaded ends. Lateral fixation is accomplished outside of the fractured bone. After fixation of the in marrow nail structure, no rotation is possible anymore, and also no axial stability is provided.

American patent publication US2011/0009865 discloses an intramedullary pin for bone fixation in a clavicula fracture. At one end, the pin is fastened using a screw threaded part, and at the other side of the fracture, the pin is fixated using a fastener in a transverse aperture in the pin.

International patent publication WO2011/060412 discloses a pre-curved intramedullary clavicle nail, which can be anchored to the bone using one or two fixation elements, such as screws.

SUMMARY OF THE INVENTION

The present invention seeks to provide an improved intramedullary device especially suited for treatment of a fracture of a long pipe bone, such as a (mid-shaft) clavicle fracture.

According to the present invention, an intramedullary device according to the preamble defined above is provided, comprising a base pin having a primary fixation element and a connection part, a secondary fixation element attachable to the connection part at one of a plurality of predetermined distances along the base pin with respect to the primary fixation element, wherein the connection part of the base pin and the secondary fixation element are rotatable with respect to each other when attached.

Due to the components of the present invention intramedullary device embodiments, once in place the connection between the two fractured clavicula parts will be rigid in the axial plane so it will prevent the mid-shaft clavicle fracture from shortening but remains free to rotate within itself to prevent hardware failure and implant migration. The surgical technique needed for implantation of the present device embodiments is minimally invasive. It is expected that time needed for the procedure is shorter and less invasive than by using the current standard therefore being more cost effective and cheaper as well.

SHORT DESCRIPTION OF DRAWINGS

The present invention will be discussed in more detail below, using a number of exemplary embodiments, with reference to the attached drawings, in which FIG. 1 shows a side view of a base pin of an embodiment of the intramedullary device according to the present invention;

DETAILED DESCRIPTION OF EXEMPLARY EMBODIMENTS

Figure 1:
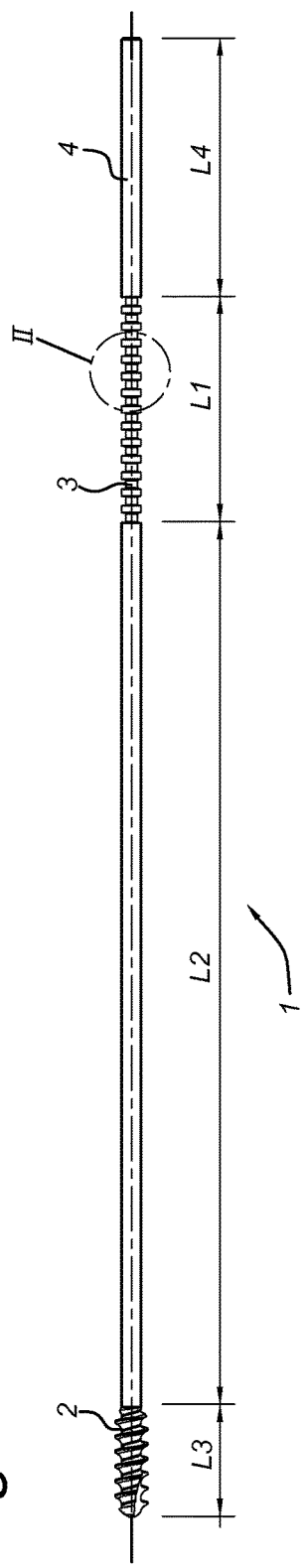
Figure 2:
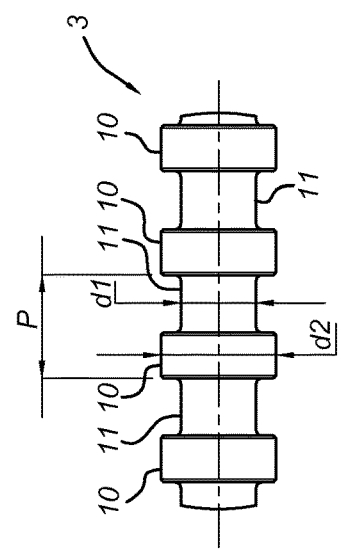
FIG. 2 shows an enlarged sectional side view of a connection part of the base pin of FIG. 1, which allows selection of an appropriate length of the intramedullary device.
Figure 3A:
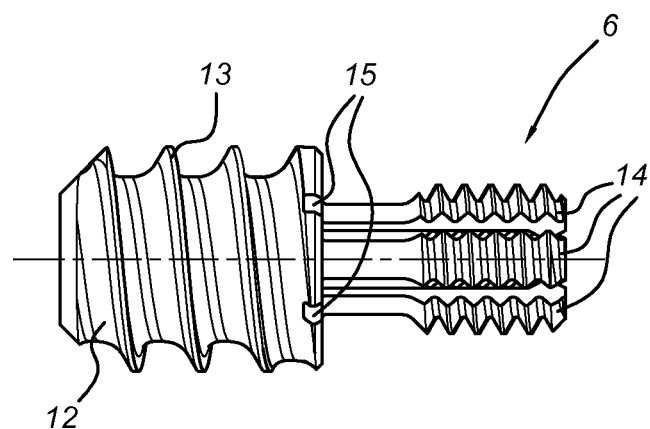
FIGS. 3a and 3b show a side view and a cross sectional view of a secondary fixation element as part of an embodiment of the intramedullary device according to the present invention.
Figure 3B:
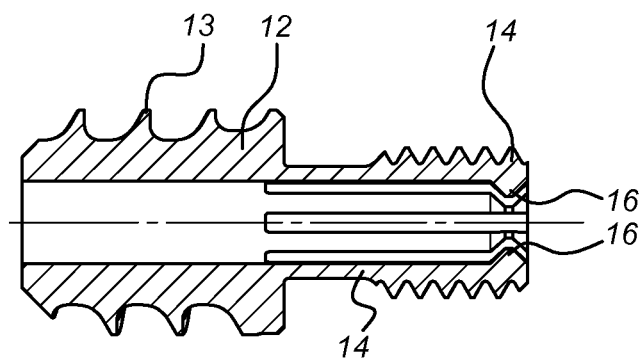

The present invention provides a number of embodiments of an intramedullary (fixation) device for mid shaft clavicle fractures (MSCF) as specific application, and more general for treatment of a fracture of a long pipe bone. Currently available intramedullary implants do not have the properties for optimal reduction and conservation of the anatomical shape and length of the clavicle when fractured. The proposed solution embodiments provide a device that is able to re-establish anatomical alignment, prevent shortening and is able to rotate freely within itself, all in a minimally invasive manner. It is expected that time needed for the procedure is shorter, the implants are cheaper, rehabilitation will be similar and therefore will be more cost-effective than by using the current standard or other minimally invasive devices.

Clavicle fractures approximately constitute for 5% of all fractures. About 69-82% of these fractures are mid-shaft clavicle fractures (MSCF). Because of the specific s-shaped anatomy and muscle insertions, about 73% of these fractures are displaced and/or shortened. These two features have been found to be poor predictors of outcome concerning non-unions, persistent posttraumatic symptoms and cosmetics in conservatively treated MSCF. Therefore, lately the tendency has been to surgically reduce and fixate MSCF if shortened more than 2 cm or displaced more than the diameter of the clavicle's shaft. The standard for these operations now is fixation using a (angle-stable) plate and screws. This method creates a rigid fixation of both fracture elements and aims for primary bone healing. It re-establishes the normal length and alignment of the clavicle. Patients are able to quickly start rehabilitating. There have been reports that operative interventions results in better rates of union, less mal-unions and increased patient satisfaction. The downsides of these procedures are a large incision and scarring, risk of infection, and need for hardware removal in about half of the patients because of irritation.

Another frequently used technique to reduce and align MSCF is by using intramedullary devices. Examples of these devices are straight rigid pins (Hagie, Knowles, Rockwood) and titanium elastic nails (TEN). The first one aims for primary bone-healing and requires an inside-out open reduction operative technique which means loss of the fracture hematoma. It has produced contradictory results. The latter aims for secondary fracture healing by not evacuating the fracture hematoma with all its bone-healing substances. TEN is minimally invasive; it requires smaller incisions. Also hardware removal if necessary is easier and less invasive. Because of the flexibility of TEN it allows itself to follow the shape of the clavicle and re-align the MSCF. Good results have been reported using TEN. The downside of TEN is that they do not protect the MSCF from shortening and subsequent forming of a possible symptomatic malunion. Other negative features of TEN are well documented implant migration because it is not fixated well within the clavicle and a high rate of implant removal after healing of the fracture has occurred.

To create an optimal method of fixating MSCF all of the issues described above need to be taken into account. The device would need specific features. It should be intramedullary so it is less invasive. An intramedullary device would also make it possible to prevent evacuation of the fracture hematoma so secondary bone-healing can be pursued. It should be flexible enough to follow the s-shaped contour of the clavicle. It has to be rigid enough to be able to re-align and prevent shortening of the MSCF. It should be fixated in both fracture elements to prevent shortening and migration. It must be simple to implant and simple to remove if necessary. If these requirements are met it is likely that this device will be superior to the current standard of plate osteosynthesis.

According to the present invention embodiments an intramedullary device for treatment of fracture of a long pipe bone (such as a mid-shaft clavicle fracture) is provided, comprising a (flexible or at least bendable) base pin 1 having a primary fixation element 2 and a connection part 3, and a secondary fixation element 6 attachable to the connection part 3 at one of a plurality of predetermined distances along the base pin with respect to the primary fixation element 2. The connection part 3 of the base pin 1 and the secondary fixation element 6 are rotatable (or rotationally free) with respect to each other when attached. The axial position of the secondary fixation element 6 with respect to the primary fixation element 2 is then fixed. This means axial stability in which the length of the base pin 1 (and the clavicle) cannot change in any of the two axial directions while at the same time the freedom to rotate within itself (i.e. locally where the secondary fixation element 6 is attached) will prevent hardware failure and subsequent implant migration and/or shortening of the (implanted) intramedullary device.

An embodiment of such an intramedullary device is shown as parts depicted in FIG. 1-4b as will be described below. FIG. 1 shows a side view of an embodiment of a base pin 1, having a total length of $l_1+l_2+l_3+l_4$ as shown. The (flexible) base-pin 1 can easily be implanted intramedullary through the clavicle's two fracture elements so alignment is obtained. The base pin 1 has a primary fixation element 2, which in the embodiment shown comprises a self-tapping threaded head end (2a), allowing fixation of the base pin in a sternal or medial end of the clavicle. By using a threaded head end 2a implantation will be more controlled and thus safer then by using TEN. The self-tapping threaded head end (2a) is provided with a blunt tip part (2b), to prevent perforation into the sterno-clavicular joint. The tip 2b is e.g. provided with a radius of 12.7 mm over 90°, when the main diameter of the base pin 1 is e.g. 2 mm. The threaded head-end 2a is provided with a screw thread having a pitch distance which is adapted for its use in anchoring the base pin 1 in the clavicle.

As shown in the embodiment of FIG. 1, the base pin 1 further comprises a handling part 4 remote from the primary fixation element 2. A special tool can e.g. be attached to this handling part 4, e.g. allowing exertion of a screwing motion to fix the primary fixation element 2 inside the clavicula bone.

In order to cater for the internal shape of the clavicula bone, the base pin 1 is bendable in a further embodiment. This can e.g. be accomplished by selecting the right material, e.g. stiff yet bendable such as AISI 304 stainless steel, in combination with a proper diameter (e.g. 2 mm). Alternatively, the base pin 1 is made of another medical grade material, such as titanium.

The secondary fixation element 6, or intra-cortical fixation device, is positioned in the dorsolateral aspect of the clavicle in use near the conoid process to allow fixation within the bone and around the base pin 1 at the appropriate length. Eventually, the base pin 1 will be cut at the appropriate length. An end cap or locking screw 7 (see below for further details thereof) may fixate the secondary fixation element 6 to the connection part 3 at the correct length and on both sides of the fractures.

As shown in the embodiment of FIG. 1, the connection part 3 is provided over a predetermined length $l_1$ of the base pin 1, remote from the primary fixation element 2 (which has a length $l_3$). The mutual distance between the first and secondary fixation elements 2, 6 can thus be selected dependent on the specific situation.

Furthermore, the connection part 3 comprises a plurality of restrictions 11 (e.g. in the form of indentations, or a stepped or sinusoid cylinder profile) having an outer diameter $d_1$ different from a local outer diameter $d_2$ of the base pin 1, indicated by surface 10. This is shown in detail in the enlarged partial view of the connection part in FIG. 2. In the embodiment shown, the outer diameter $d_1$ is smaller (e.g. 1.3 mm) than the local outer diameter $d_2$ (e.g. 2 mm), which can e.g. be accomplished by a simple milling process step of the base pin 1.

Figure 4A:
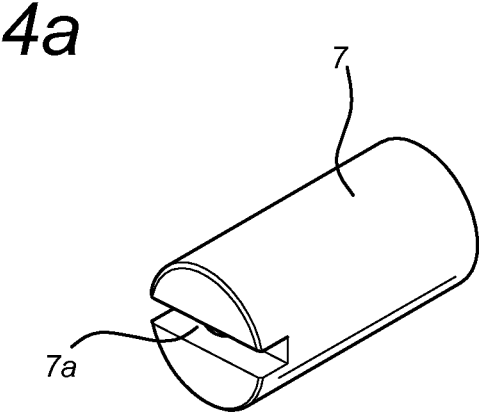
FIGS. 4a and 4b show a perspective view and a cross sectional view of an end cap to be used in conjunction with the secondary fixation element of FIGS. 3a and 3b.
Figure 4B:
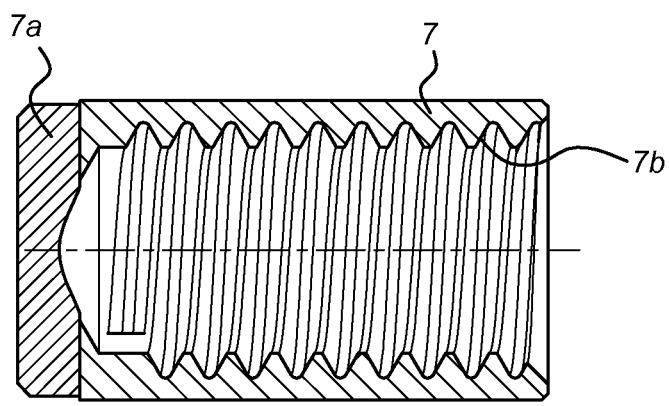

An embodiment of the secondary fixation element 6 is shown in more detail in aside view in FIG. 4a and in a cross sectional view in FIG. 4b. In order to be able to shift or slide the secondary fixation element 6 over the handling part 4 and the connection part 3, the secondary fixation element 6 has a bore with an inner diameter which is larger than an outer diameter of the base pin 1 in a further embodiment (e.g. 2.2 mm and 2.0 mm).

In a further embodiment, the secondary fixation element 6 comprises a self tapping (and intra-cortical) threaded part 12, allowing to fixate the secondary fixation element 6 to the other part of the (fractured) clavicula. The size and pitch of the threaded part 12 may be similar to the size and pitch of the threaded head end 2a of the primary fixation element 2. As shown most clearly in the side view of FIG. 3a, the secondary fixation element 6 is provided with a plurality of slots 15 in the self-tapping threaded part 12. These slots 15 allow fixation of the secondary fixation element 6 using a special tool sliding over entire exposed part of the base pin 1, as will be discussed in more detail below.

To ascertain that the primary and secondary fixation elements 2, 6 stay at the set distance from each other, the secondary fixation element 6 comprises a locking end 17 having a plurality of resilient legs 14 each having an inwardly extending end part 16 in a further embodiment. The resilient legs 14 press the inwardly extending parts 16 into the restrictions 11 of the connection part 3, thereby fixing the set distance, yet allowing rotation. Alternatives would e.g. be to use another pressure exerting element, e.g. one or more leaf springs, etc.

To lock the secondary element 6 into position with respect to the connection part 3, in a further embodiment the locking end 17 is provided with an outer thread and the secondary fixation element 6 further comprises a locking screw 7 as implementation of the end cap 7. A perspective view of the locking screw is shown in FIG. 4a, and a cross sectional view in FIG. 4b. The locking screw 7 is provided with an internal screw thread 7b matching the external screw thread on the resilient legs 14, and furthermore comprises a slit 7a allowing a screw driver type of installation of the locking screw 7.

Figure 5:
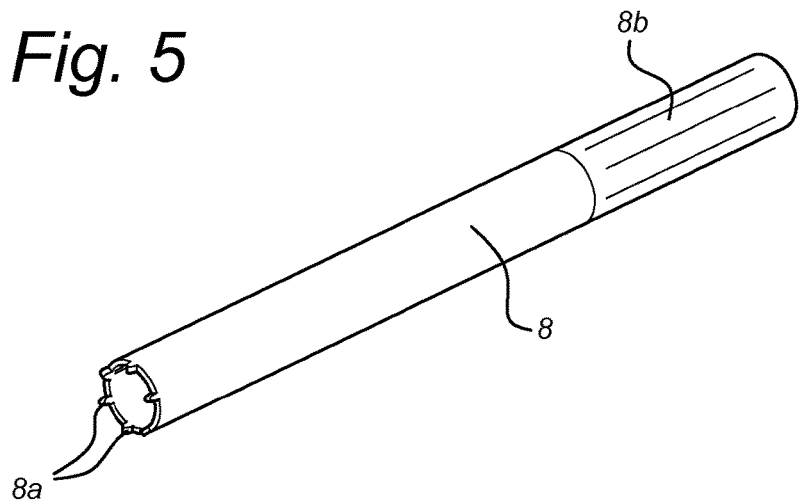
FIG. 5 shows a perspective view of a first tool to be used with the intramedullary device according to the present invention embodiments.

In a further aspect, the present invention also relates to a kit for a fracture of a long pipe bone, such as a clavicle fracture, comprising an intramedullary device according to any one of the embodiments as described above. Furthermore, the kit comprises a first tool for fixing the primary fixation element 2 of the base pin 1 in a medial part of the long pipe bone/clavicula (e.g. using a handle bar attached to the handling part 4), and a second tool 8 for fixing the secondary fixation element 6 to a further part of the long pipe bone/clavicula. An embodiment of this second tool is shown in the perspective view of FIG. 5, and is e.g. shaped as a hollow cylinder, able to slide over the still remaining parts of the base pin 1. The second tool 8 is provided with extending parts 8a, matching the slots 15 on the secondary fixation element 6, and allowing to exert sufficient torque to properly fixate the secondary fixation element 2 in the clavicula.

Figure 6:
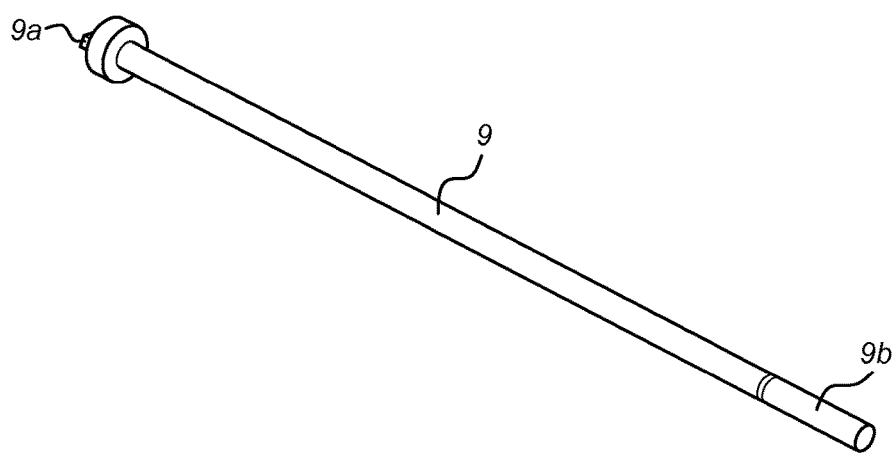
FIG. 6 shows a perspective view of a second tool to be used with the intramedullary device according to the present invention embodiments.

Once the secondary fixation element 6 is secured in the long pipe bone/clavicula, the base pin 1 can be cut to length (e.g. at one of the restrictions 11 of the connection part 3), e.g. using a generally available (surgical) cutting tool, or a specific cutting tool being part of the kit. After that, the locking screw 7 can be positioned over the resilient legs 14 of the secondary fixation element, and fastened using a third tool 9 for attaching the secondary fixation element 6 to the connection part 3 of the base pin 1. The third tool is shown in perspective in FIG. 6 and is provided with a first end having a screwdriver type (flat) head 9a, matching the slit 7a of the locking screw 7. Furthermore, the third tool 9 may be provided with a handling part 9b, similar to the handling part 4 of the base pin 1, allowing e.g. to attach a handle to allow a screwing motion of the third tool 9.

In summary, the innovative aspect of the device developed lies in being an intramedullary device that is able to re-establish anatomical alignment, prevent shortening and its ability to rotate freely within itself. Especially the latter is the key to the new intramedullary device for MSCF, but also very usable for treatment of other fractures involving long pipe bones. This should be made possible by its design as summarized above and as shown in the drawing embodiments.

The present invention embodiments have been described above with reference to a number of exemplary embodiments as shown in the drawings. Modifications and alternative implementations of some parts or elements are possible, and are included in the scope of protection as defined in the appended claims.

The invention claimed is:

1. An intramedullary device for treatment of a fracture of a long pipe bone, comprising:
    a base pin having a primary fixation element and a connection part; and
    a secondary fixation element attachable to the connection part at one of a plurality of predetermined distances along the base pin with respect to the primary fixation element,
    wherein the secondary fixation element comprises a locking end for preventing axial movement of the first fixation element relative to the second fixation element when attached, while allowing the connection part of the base pin and the secondary fixation element to rotate with respect to each other, and
    wherein the locking end has a plurality of resilient legs each having an inwardly extending end part.

2. The intramedullary device of claim 1, wherein the connection part is provided over a predetermined length of the base pin.

3. The intramedullary device of claim 1, wherein the connection part comprises a plurality of restrictions having an outer diameter different from a local outer diameter of the base pin.

4. The intramedullary device of claim 1, wherein the secondary fixation element has a bore with an inner diameter which is larger than an outer diameter of the base pin.

5. The intramedullary device of claim 1, wherein the locking end is provided with an outer thread and the secondary fixation element further comprises an end cap.

6. The intramedullary device of claim 1, wherein the secondary fixation element comprises a self-tapping threaded part.

7. The intramedullary device of claim 6, wherein the secondary fixation element is provided with a plurality of slots in the self-tapping threaded part.

8. The intramedullary device of claim 1, wherein the primary fixation element comprises a self-tapping threaded head end.

9. The intramedullary device of claim 8, wherein the self-tapping threaded head end is provided with a blunt tip part.

10. The intramedullary device of claim 1, wherein the base pin further comprises a handling part remote from the primary fixation element.

11. The intramedullary device of claim 1, wherein the base pin is bendable.

12. A kit for a fracture of a long pipe bone, such as a clavicle fracture, comprising
    the intramedullary device of claim 1,
    a first tool for fixing the primary fixation element of the base pin in a medial part of the long pipe bone,
    a second tool for fixing the secondary fixation element to a further part of the long pipe bone, and
    a third tool for attaching the secondary fixation element to the connection part of the base pin.

13. The kit of claim 12, further comprising a cutting tool for cutting the connection part to a final length of the base pin.

14. The kit of claim 12, wherein the connection part is provided over a predetermined length of the base pin.

15. The kit of claim 12, wherein the connection part comprises a plurality of restrictions having an outer diameter different from a local outer diameter of the base pin.

16. The kit of claim 12, wherein the secondary fixation element has a bore with an inner diameter which is larger than an outer diameter of the base pin.

17. The kit of claim 12, wherein the locking end is provided with an outer thread and the secondary fixation element further comprises an end cap.

18. The kit of claim 12, wherein the secondary fixation element comprises a self-tapping threaded part.

19. The kit of claim 18, wherein the secondary fixation element is provided with a plurality of slots in the self-tapping threaded part.

20. The kit of claim 12, wherein the primary fixation element comprises a self-tapping threaded head end.

21. The kit of claim 20, wherein the self-tapping threaded head end is provided with a blunt tip part.

22. The kit of claim 12, wherein the base pin further comprises a handling part remote from the primary fixation element.

23. The kit of claim 12, wherein the base pin is bendable.

* * * * *